United States Patent [19]
Babler

[11] Patent Number: 5,847,185
[45] Date of Patent: Dec. 8, 1998

[54] C-15 PHOSPHONATE REAGENT COMPOSITIONS AND METHODS OF SYNTHESIZING THE SAME

[75] Inventor: James H. Babler, Chicago, Ill.

[73] Assignee: Loyola University of Chicage, Chicago, Ill.

[21] Appl. No.: 975,819

[22] Filed: Nov. 21, 1997

[51] Int. Cl.$^6$ .............................. C07F 9/6574; C07F 9/40
[52] U.S. Cl. .............................. 558/83; 558/137; 558/217
[58] Field of Search ................................ 558/83, 137, 217

[56] References Cited

U.S. PATENT DOCUMENTS

| | | | |
|---|---|---|---|
| 3,197,497 | 7/1965 | Mark | 260/461 |
| 4,916,250 | 4/1990 | Babler | 558/217 |
| 5,061,819 | 10/1991 | Babler | 558/87 |
| B1 4,916,250 | 6/1993 | Babler | 558/217 |

OTHER PUBLICATIONS

W. Oroshnik, et al., "The Nef Reaction with α, β–Unsaturated Ketones" *J. Am. Chem. Soc.*, 71, 2062 (1949).

Johnson and Schneider, "β–Carbethoxy–γ,γ–Diphenylvinylacetic Acid" *Org. Synth.*, 30, 18 (1950).

J. Michalski, et al., "Anhydrides of Organophosphorus Acids. Part II. The Synthesis of Tri– and Tetra–alkyl Esters of Phosphorous Phosphoric Anhydride" *J. Chem. Soc.*, 4904 (1961).

M.P. Savage and S. Trippett, "The Rearrangement of Alk–2–enyl Diphenylphosphinites" *J.Chem.Soc.(C)* 1842 (1996).

M. Freifelder, Practical Catalytic Hydrogenation: Techniques and Applications (Wiley–Interscience, New York, 1971), pp. 143–144.

M. M. Midland, "Preparation of Monolithium Acetylide in Tetrahydrofuran. Reaction with Aldehydes and Ketones." *J. Org. Chem.*, 40, 2250 (1975).

H. Altenbach, et al., "Phosphor–und Schwefelsubstituierte Allene in der Synthese I: Einfache Synthese von β–Ketophosphonaten aus 1–Alkin–3–Olen" *Tetrahedron Lett.22*, 5157 (1981).

M. J. Szwedo, Jr., Studies Directed Towards The Total Synthesis of Retinoids, Ph.D. Dissertation, Loyola University of Chicago, pp. 24 & 57–59 (1983).

C. Palmer, et al., "Selective Catalytic Hydrogenation of an Olefin Moiety in the Presence of a Terminal Alkyne Function" *Tetrahedron Lett.*, 20, 2857 (1990).

Babler and Schlidt, "An Expedient Route to a Versatile Intermediate for the Steroselective Synthesis of all–trans–Retinoic Acid and beta–Carotene" *Tetrahedron Lett.*, 33, 7697 (1992).

B. C. Ranu, et al., "Regio– and Stereoselective Hydrogenation of Conjugated Carbonyl Compounds via Palladium Assisted hydrogen Transfer by Ammonium Formate" *Tetrahedron Lett.*, 35, 8649 (1994).

*Primary Examiner*—Michael G. Ambrose
*Attorney, Agent, or Firm*—Marshall, O'Toole, Gerstein, Murray & Borun

[57] ABSTRACT

Allenic phosphonate reagent compositions are described which have the formula:

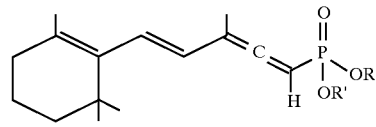

wherein R and R'=$C_1$–$C_4$ alkyl groups, or R, R'=$(CH_2)_n$ (n=2 or 3) or $[CH_2C(CH_3)_2CH_2]$.

Also described are methods for forming such allenic phosphonates from ethynyl-β-ionol, and for converting these allenic compounds to allylic phosphonate compounds which can be used in the synthesis of a variety of biologically-active materials.

19 Claims, No Drawings

C-15 PHOSPHONATE REAGENT COMPOSITIONS AND METHODS OF SYNTHESIZING THE SAME

BACKGROUND OF THE INVENTION

1. Field of the Invention

The present invention describes novel phosphonate reagent compositions of the formula:

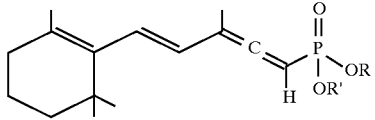

wherein R and R'=$C_1$–$C_4$ alkyl groups, or R, R'=$(CH_2)_n$ (n=2 or 3) or $[CH_2C(CH_3)_2CH_2]$.

Also described are novel methods for forming allenic C-15 phosphonate reagent compositions (1) from ethynyl-β-ionol [IUPAC name: 3-methyl-1-(2,6,6-trimethylcyclohex-1-enyl)pent-1-en-4-yn-3-ol].

Allenic reagent compositions (1) can be partially hydrogenated to form allylic C-15 phosphonate compounds of the formula:

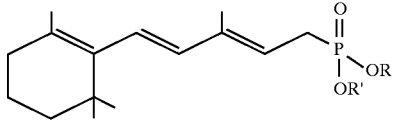

Phosphonate compounds (2) can be employed as precursors to a variety of biologically-active materials, including 13-cis retinoic acid Accutane®, Retin-A® and beta-carotene.

2. Description of Related Art (a) Prior Art Process for Preparation of C-15 Phosphonate Compounds (2).

U.S. Pat. Nos. 4,916,250 and 5,061,819 (James H. Babler) describe processes for forming C-15 phosphonate compounds (2) from β-ionone (3) and for using such compounds in the one-step synthesis of vitamin A, Retin-A®, the anti-acne drug Accutane®, and beta-carotene. The complete disclosure of these two patents is incorporated by reference herein. An illustrative, multi-step procedure for forming an allylic C-15 phosphonate compound (2) in accordance with the above patents is as follows:

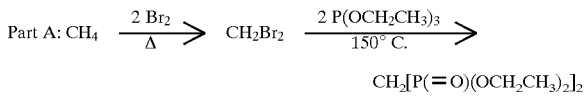

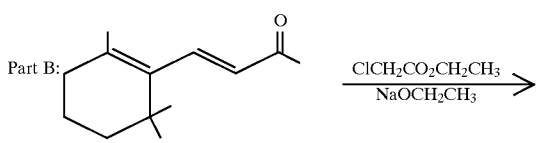

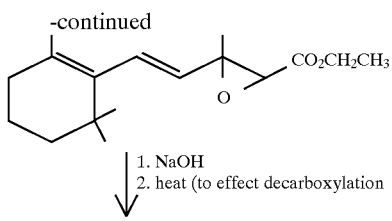

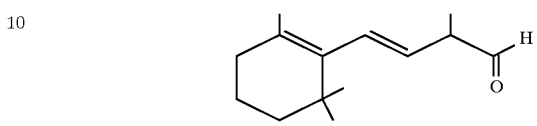

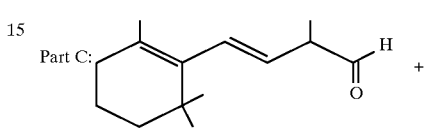

Part C:

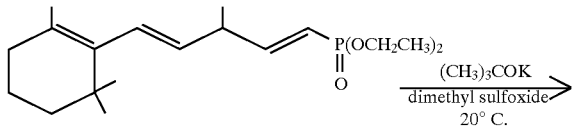

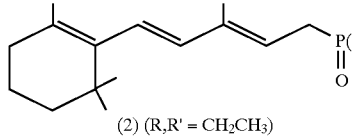

(2) (R,R' = $CH_2CH_3$)

The above route has been successfully used to synthesize C-15 phosphonate reagents (2) from β-ionone (3). However, aspects of the synthesis detract from its adaptation as a commercial procedure:

1. The synthesis requires the use of two equivalents of a trialkyl phosphite (e.g., triethyl phosphite), thereby generating a relatively large amount of phosphate waste.

2. Starting from β-ionone (3), the process requires the use of two costly raw materials: dibromomethane and (to a lesser extent) ethyl chloroacetate.

3. Most importantly, the above process requires too many reaction steps (approximately 7) to convert β-ionone (3) to C-15 phosphonate (2).

(b) Prior Art Processes For Forming 3° Propargylic Alcohols.

The first step in a preferred method for preparing the compounds of the present invention involves the addition of acetylide to β-ionone to form a 3° propargylic alcohol (4). Procedures for synthesizing a 3° propargylic alcohol from β-ionone are described in the literature: 86–95% yield using lithium acetylide; 77% yield using calcium acetylide; or 92% yield using HC≡CMgCl. M. M. Midland, *J.Org.Chem.* 1975, 40, 2250; W.Oroshnik and A. D. Mebane, *J.Am.Chem.Soc.*, 1949, 71, 2062.

(c) Prior Art Processes For Converting 3° Propargylic and Allylic Alcohols to Allenic and Allylic Phosphonates.

The second step in the preparation of phosphonate reagent compositions (1) is a novel process wherein ethynyl-β-ionol is reacted with a dialkyl chlorophosphite. Processes wherein structurally-simple 3° propargylic alcohols have been converted to allenic phosphonates have been described:

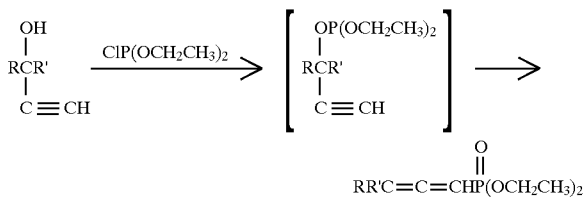

For examples of the above reaction, see: H. J. Altenbach and R. Korff, *Tetrahedron Lett.*, 1981, 22, 5175 and U.S. Pat. No. 3,197,497.

In a similar process, 3° allylic alcohols have been converted into allylic phosphonates:

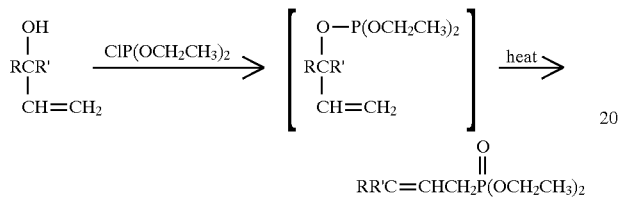

However, an attempt to convert vinyl-β-ionol (6):

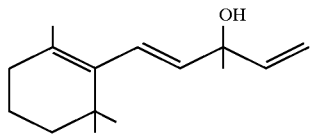

(obtained by treatment of β-ionone with vinylmagnesium chloride) to a C-15 phosphinite reagent similar to phosphonate compound (2) proceeded poorly (0–8% yield of an allylic phosphinite compound). M. P. Savage and S. Trippett, *J.Chem.Soc.(C)* 1966, 1842.

Similarly, ethynyl-β-ionol (4) has been reported to undergo dehydration when treated (0° C. to room temperature) with phosphorous oxychloride and a non-nucleophilic base (e.g., a tertiary amine such as pyridine or triethylamine):

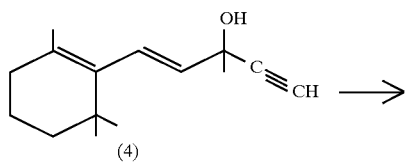

See, M. J. Szwedo, Jr., STUDIES DIRECTED TOWARDS THE TOTAL SYNTHESIS OF RETINOIDS, Ph.D. Dissertation, Loyola University of Chicago, 1983, pages 24 & 57–59.

SUMMARY OF THE INVENTION

The present invention describes novel allenic phosphonate reagent compositions (1) which can be synthesized in two steps from β-ionone (3). When R and R' are alkyl groups having up to four carbon atoms, the compounds of the invention are systematically named as esters of an alkenylphosphonic acid. For example, when R=R'=ethyl, the compound is named:

3-methyl-5-(2,6,6-trimethyl-1-cyclohexen-1-yl)-1,2,4-pentatrienylphosphonic acid, diethyl ester.

Other compounds within the scope of the present invention include:

3-methyl-5-(2,6,6-trimethyl-1-cyclohexen-1-yl)-1,2,4-pentatrienylphosphonic acid, dimethyl ester;

3-methyl-5-(2,6,6-trimethyl-1-cyclohexen-1-yl)-1,2,4-pentatrienylphosphonic acid, diisopropyl ester;

3-methyl-5-(2,6,6-trimethyl-1-cyclohexen-1-yl)-1,2,4-pentatrienylphosphonic acid, dipropyl ester;

3-methyl-5-(2,6,6-trimethyl-1-cyclohexen-1-yl)-1,2,4-pentatrienylphosphonic acid, dibutyl ester; and 3-methyl-5-(2,6,6-trimethyl-1-cyclohexen-1-yl)-1,2,4-pentatrienylphosphonic acid, ethyl methyl diester.

Phosphonate reagents (1) also include allenic C-15 phosphonate compounds in which R and R' form part of a 5- or 6-membered heterocyclic ring:

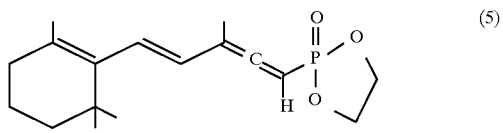

Unlike their non-heterocylic counterparts, these C-15 compounds are not named as diesters of a phosphonic acid. For example, when R,R'=CH$_2$ CH$_2$ [i.e., compound (5)], the ester is named 2-[3-methyl-5-(2,6,6-trimethyl-cyclohex-1-enyl) penta-1,2,4-trienyl]-1,3,2-dioxaphospholan-2-one.

An outline of a preferred route for forming allylic C-15 phosphonate compounds (2) comprises steps (a) through (c) as follows:

(a) 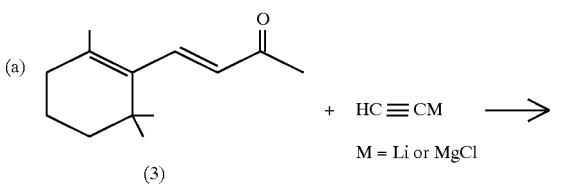

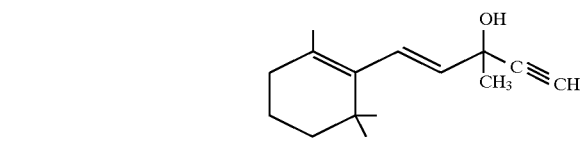

(b) 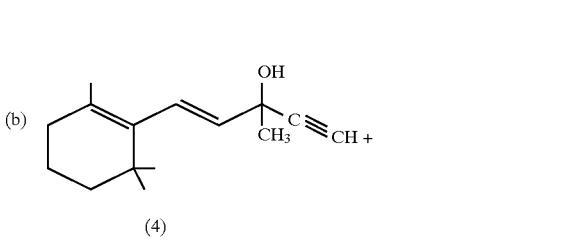

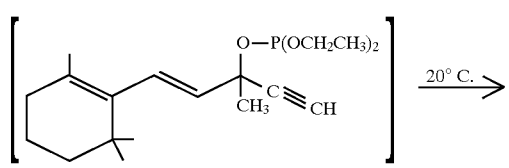

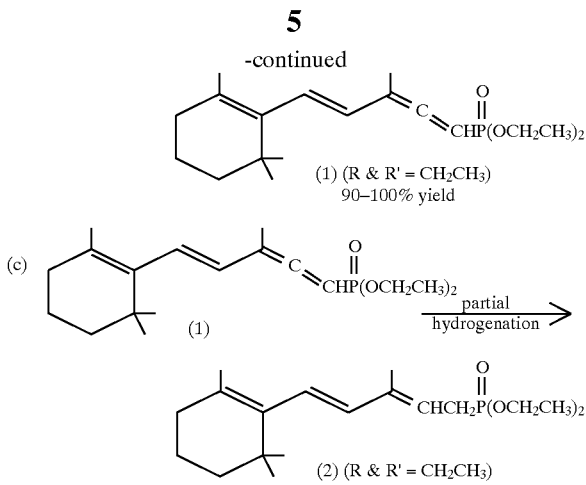

Novel allenic phosphonates (1) are formed in the course of this synthesis.

As mentioned previously, step (a) of the above procedure—the formation of the 3° propargylic alcohol, ethynyl-β-ionol [IUPAC name: 3-methyl-1-(2,6,6-trimethylcyclohex-1-enyl) pent-1-en-4-yn-3-ol]—is suggested in the prior art. M. M. Midland, *J.Org.Chem.* 1975, 40, 2250; W.Oroshnik and A. D. Mebane, *J.Am.Chem.Soc.*, 1949, 71, 2062.

Step (b) of the procedure—the conversion of ethynyl-β-ionol (4) to allenic phosphonates (1)—utilizes a reagent with a phosphorus-chlorine bond in the presence of a 3° amine. This conversion requires:

(A) ethynyl-β-ionol in an aprotic organic solvent;

(B) the presence of at least one molar equivalent of a non-nucleophilic base: tertiary amines such as pyridine or triethylamine, $Na_2CO_3$, and $K_2CO_3$ are especially preferred; and (C) addition of one molar equivalent of a chlorophosphite reagent, $(RO)_2PCl$, wherein the R groups independently represent $C_1$ to $C_4$ alkyl or wherein the R groups, taken together, form part of a 5- or 6-member ring to a mixture of (A) and (B): preferred phosphite reagents include diethyl chlorophosphite and 2-chloro-1,3,2-dioxaphospholane.

Step (b) proceeds at reaction temperatures from approximately 0° C. to room temperature, although higher temperatures can be employed. In a preferred method, the chlorophosphite reagent is added, dropwise, to a stirred reaction mixture which is maintained under an atmosphere of a non-reactive gas (e.g., nitrogen gas). The reaction proceeds rapidly (less than one hour). Upon completion, the addition of a small amount of water to the reaction mixture will destroy any unreacted chlorophosphite reagent.

The chlorophosphite reagent utilized in step (b) can be prepared by treating $PCl_3$ with 2 equivalents of alcohol (e.g., ethyl alcohol) in a nonpolar solvent as described by J. Michalski, et. al. in *J.Chem.Soc.*, 1961, 4904. Alternatively, the desired transformation can be effected by adding $PCl_3$ to the mixture of (A) and (B), followed by the addition of two equivalents of alcohol.

Allenic reagent compositions (1) can be partially hydrogenated to form allylic C-15 phosphonate compounds (2) as depicted in step (c), supra. Initial, unsuccessful attempts to selectively reduce the double bond between C-1 and C-2 (which is subject to the steric effects of the bulky phosphonate group) involved the use of a procedure reported by B. C. Ranu and A. Sarkar [*Tetrahedron Lett.*, 1994, 35, 8649] for the regioselective hydrogenation of conjugated carbonyl compounds. In accordance with the procedure recommended in this reference, 1 mmole of C-15 allenic phosphonate (1) was treated with 6 mmoles of ammonium formate and 30 mg of 10% Pd-C in methyl alcohol to effect the desired hydrogenation. Although the double bond between C-1 and C-2 was hydrogenated under these conditions, simultaneous reduction of the disubstituted double bond between C-4 and C-5 also occurred. Indeed, due to the influence of the phosphonate group, the disubstituted double bond between C-4 and C-5 appeared easier to hydrogenate than the olefinic linkage between C-1 and C-2. C. J. Palmer et al. have reported that olefin moieties can be selectively hydrogenated in the presence of the easily reduced terminal alkyne functionality if a bulky substituent is bonded to the latter [*Tetrahedron Lett.*, 1990, 31, 2857]. The double bond between C-1 and C-2 is part of an allenic moiety (i.e., a 1,2-propadienyl group), the hydrogenation of which frequently resembles that of acetylene functionality. See, M. Freifelder, PRACTICAL CATALYTIC HYDROGENATION: TECHNIQUES AND APPLICATIONS (Wiley-Interscience, New York, 1971), pp. 143–44.

It was found that step (c) of the reaction—the partial hydrogenation of allenic reagent compositions (1) to allylic C-15 phosphonate compounds (2)—could be accomplished by using one equivalent of ammonium formate and 10% Pd-C as a catalyst in an alcohol solvent; methyl alcohol is especially preferred. The hydrogenation reaction occurs at temperatures in excess of room temperature. The reaction proceeds slowly unless the reaction mixture is stirred vigorously. Heating a vigorously stirred reaction mixture to a temperature between about 60° C. and 65° C. for a period of 2.5 hours resulted in the partial hydrogenation of the desired double bond between C-1 and C-2, while preserving the double bond between C-4 and C-5.

DETAILED DESCRIPTION OF THE INVENTION

The following examples are presented for purposes of illustration and should not be construed as limiting the invention which is delineated in the claims.

EXAMPLE I

Preparation of 3-Methyl-1-(2,6,6-trimethyl-1-cyclohexen-1-yl)-1-penten-4-yn-3-ol by Treatment of beta-Ionone With Ethynylmagnesium Chloride 20 ml of 0.5M solution of ethynylmagnesium chloride (10 mmoles) in tetrahydrofuran (purchased from Aldrich Chemical Co., Milwaukee, Wis.) was added to a 100 ml 3-neck reaction flask fitted with an addition funnel and an adapter connected to an apparatus similar to that described by Johnson and Schneider [*Org. Synth*, 30, 18 (1950)] so that the mixture in the flask could be protected from atmospheric moisture, et al. throughout the course of the reaction. After sweeping the system briefly with a stream of nitrogen gas and placing the flask in an ice-water bath (0° C.), a solution of 1.00 ml (4.91 mmoles) of beta-ionone (purchased from Aldrich Chemical Co.) in 2.50 ml of anhydrous tetrahydrofuran was added dropwise over 5 minutes to the stirred Grignard reagent. The resulting mixture was stirred at 0° C. for an additional 75 minutes; after which it was diluted with 5 ml of hexane and the excess organometallic reagent was destroyed by slow, dropwise addition of 8 ml of saturated aqueous ammonium chloride. After allowing the mixture to warm to room temperature, it was diluted with 50 ml of 1:1 (v/v) hexane: ether and 200 ml of saturated brine mixed with 5 ml of 2M aqueous HCl. After separation from the aqueous layer, the organic layer was washed with saturated brine (2×150 ml), dried over anhydrous magnesium sulfate, and subsequently filtered. Removal of the volatile organic solvents by evaporation at reduced pressure and subsequent evaporative ("Kugelrohr oven") distillation in the presence of 10 mg of powdered $CaCO_3$ afforded 984 mg (92% yield) of the named unsaturated alcohol: boiling point 92°–100° C. (bath temperature, 0.30 mm). The identity and purity of this compound was ascertained by IR and proton NMR analysis (recorded in $CDCl_3$ solution at 400 MHZ). The latter spectrum exhibited two doublets (J=16 Hz) at δ 6.417 and 5.56 (C-1 and C-2 vinyl H's), a singlet at 2.59 (C≡CH), a broad singlet at δ 2.202 (OH), a broad singlet at δ1.673 (ring vinyl methyl), a singlet at δ1.613 ($CH_3$ bonded to C-3), and a singlet at δ 1.00 [$C(CH_3)_2$]. Alternate routes to this same alkynol can be found in M. M. Midland, *J. Org. Chem.*, 40, 2250 (1975) and W. Oroshnik, et al., *J. Am. Chem. Soc.*, 71, 2062 (1949).

EXAMPLE II

Preparation of 3-Methyl-5-(2,6,6-trimethyl-1-cyclohexen-1-yl)-1,2,4-pentatrienylphosphonic acid, Dieth To a 15 ml 2-neck reaction flask fitted with an adapter connected to an apparatus similar to that described by Johnson and Schneider [*Org. Synth.*, 30, 18 (1950)] so that the mixture in the flask could be protected from atmospheric moisture, et al. throughout the course of the reaction were added 304 mg (1.39 mmoles) of distilled alkynol prepared as described in Example I, 0.35 ml (2.5 mmoles of triethylamine, purchased from Aldrich Chemical Co., Milwaukee, Wis.), and 2.50 ml of dichloromethane (A.C.S. reagent-grade, purchased from Aldrich Chemical Co.). After placing the flask in an ice-water bath (0° C.), 0.25 ml (1.73 mmoles) of diethyl chlorophosphite (95%, purchased from Aldrich Chemical Co.) was added dropwise via syringe while simultaneously maintaining the stirred reaction mixture under a gentle stream of nitrogen gas. The resulting mixture was stirred at 0° C. for an additional 10 minutes and subsequently at room temperature for 60 minutes. The mixture was then cooled to approximately 0° C. by means of an external ice-water bath, and 0.10 ml of water was added to destroy any unreacted diethyl chlorophosphite. After dilution of the mixture with 30 ml of 2:1 (v/v) hexane: dichloromethane, the organic layer was washed in successive order with 20 ml portions of 10% aqueous sodium chloride and saturated brine. The organic extracts were then dried over anhydrous magnesium sulfate and subsequently filtered. Removal of the volatile organic solvents by evaporation at reduced pressure, subsequent addition of 5 ml of benzene to the residual material, and removal of the benzene accompanied by trace amounts of triethylamine under reduced pressure afforded 440 mg (93% yield) of the named phosphonate. The identity and purity of this compound was ascertained by IR (1940 $cm^{-1}$, C═C═C) and proton NMR analysis (recorded in $CDCl_3$ solution at 400 MHZ). The latter spectrum exhibited two doublets (J=17 Hz) at δ 6.08 and 5.92 (C-4 and C-5 vinyl hydrogens), a broad absorption at δ 5.47 (C-1 vinyl H), a multiplet at δ 4.105 (two $OCH_2$ moieties), a broad singlet at δ 1.93 ($CH_3$ bonded to C-3), a broad singlet at δ 1.68 (ring vinyl methyl), and a singlet at δ 1.003 [$C(CH_3)_2$].

NOTE: In lieu of purchasing diethyl chlorophosphite from Aldrich Chemical Co., it can be prepared from phosphorus trichloride and ethyl alcohol in accordance with a procedure suggested by J. Michalski, et al., *J. Chem. Soc.*, 4904 (1961).

EXAMPLE III

Preparation of 3-Methyl-5-(2,6,6-trimethyl-1-cyclohexen-1-yl)-2,4-pentadienylphosphonic Acid, Diethyl Ester To a 25 ml 1-neck reaction flask fitted with a reflux condenser connected to an apparatus similar to that described by Johnson and Schneider [*Org, Synth.*, 30, 18 (1950)] so that the mixture in the flask could be protected from atmospheric moisture, et al. throughout the course of the reaction were added 185 mg (0.547 mmole) of allenic phosphonate produced in accordance with Example II, 4.00 ml of methyl alcohol (HPLC-grade, purchased from Aldrich Chemical Co.), 45 mg (0.71 mmole) of ammonium formate (purchased from Aldrich Chemical Co.), and 20 mg of 10% Pd-C (available from Aldrich Chemical Co.). After sweeping the system briefly with nitrogen gas, the mixture was heated at 60°–65° C. (external oil bath temperature) for 2.5 hours.

NOTE: This reduction proceeds quite slowly unless the mixture is stirred vigorously throughout the course of the reaction. After cooling the mixture to room temperature, the product was isolated by dilution of the reaction mixture with 25 ml of 4:1 (v/v) ether: dichloromethane and removal of the palladium catalyst by filtration through a small pad of Hyflo Super-Cel® filtering aid. The filtrate was subsequently washed with saturated brine (2×50 ml), then dried over anhydrous magnesium sulfate and filtered. Removal of the ether and dichloromethane by evaporation at reduced pressure afforded 177 mg (95% yield) of the named allylic phosphonate, the identity of which was confirmed by comparison of its proton NMR spectrum with that previously reported by Babler and Schlidt, *Tetrahedron Lett.*, 33, 7697 (1992). This allylic phosphonate has previously been used in a synthesis of beta-carotene [Example XV in U.S. Pat. No. 4,916,250 (Apr. 10, 1990)].

The purity of this product was ascertained by IR (absence of the C═C═C absorption at 1940 $cm^{-1}$) and proton NMR analysis (recorded in $CDCl_3$ solution at 400 MHZ). The latter spectrum indicated that the product was a 1:2 mixture of E:Z stereoisomers ($C_2$–$C_3$ double bond), both of which can be used in a synthesis of beta-carotene since the Z stereoisomer isomerizes to the corresponding E stereoisomer under the reaction conditions (e.g., alkoxide base in dimethyl sulfoxide solution) utilized in the next step. The NMR spectrum of this allylic phosphonate was characterized by the following signals: two doublets (J=16 Hz) at δ 6.34 and 6.197 (C-4 and C-5 vinyl hydrogens); 2.73 ($CH_2$ P, dd, $J_{H-H}$=8 Hz, $J_{P-H}$=23 Hz); 1.915 (d, J=5 Hz, $CH_3$ bonded to C-3,Z stereoisomer); 1.83 (d, J=3 Hz, $CH_3$ bonded to C-3,E stereoisomer); 1.71 (s, ring vinyl $CH_3$Z stereoisomer); and 1.68 (s, ring vinyl $CH_3$, E stereoisomer).

NOTE: If one uses an excess (e.g., 6 molar equivalents) of ammonium formate to effect this reduction, in accordance with a procedure suggested by B. C. Ranu, et al., *Tetrahedron Lett.*, 35, 8649 (1994), over-reduction of the starting material occurs, as shown by the absence of proton NMR signals between δ 6.0–7.

EXAMPLE IV

Preparation of 2-[3-Methyl-5-(2,6,6-trimethyl-1-cyclohexen-1-yl) penta-1,2,4-trieny1]-1,3,2-dioxaphospholan-2-one The reaction was conducted in the manner described in the procedure of Example II using the following reagents: 301 mg (1.38 mmoles) of distilled 3-methyl-1-(2,6,6- trimethyl-1-cyclohexen-1-yl)-1-penten-4-yn-3-ol (produced in accordance with Example I), 0.35 mL (2.5 mmoles) of triethylamine, 2.50 mL of dichloromethane (A.C.S. reagent-grade), and 150 microliters (1.69 mmoles) of 2-chloro-1,3,2-dioxaphospholane (purchased from Aldrich Chemical Co., Milwaukee, Wis.). Isolation of the product as described in the procedure of Example II afforded 406 mg (95% yield) of the named allenic phosphonate. The identity and purity of this compound was ascertained by IR (1940 $cm^{-1}$, C=C=C) and proton NMR analysis (recorded in $CDCl_3$ solution at 400 MHz). The latter spectrum exhibited two doublets (J=16 Hz) at δ δ6.10 and 5.90 (C-4 and C-5 vinyl H's), a broad singlet at δ5.55 (C-1 vinyl H), and two multiplets at δ 4.43 and 4.17 ($OCH_2CH_2O$).

EXAMPLE V

Selective Hydrogenation of 2-[3-Methyl-5-(2,6,6-trimethyl-1-cyclohexen-1-yl) penta-1,2,4-trienyl]-1,3,2-dioxaphospholan-2-one The reaction was conducted in the manner described in the procedure of Example III using the following reagents: 154 mg (0.50 mmole) of the above-named allenic phosphonate (produced in accordance with Example IV), 41 mg (0.65 mmole) of ammonium formate, 4.0 mL of methyl alcohol (HPLC-grade), and 25 mg of 10% Pd-C. Isolation of the product as described in the procedure of Example III afforded 119 mg (70% yield) of a C-15 allylic phosphonate that can be used in the synthesis of retinoids (e.g., vitamin A) and beta-carotene. IR (3390 $cm^{-1}$, OH) and proton NMR analysis (400 MHz) indicated that the latter phosphonate was not the anticipated 2-[3-methyl-5-(2,6,6-trimethyl-1-cyclohexen-1-yl) penta-2,4,dienyl]-1,3,2-dioxaphospholan-2-one, but instead was 3-methyl-5-(2,6,6-trimethyl-1-cyclohexen-1-yl)-2,4-pentadienylphosphonic acid, beta-hydroxyethyl methyl diester. The latter's formation can be explained by a facile methanolysis of the strained heterocyclic ring (i.e., a 1,3,2-dioxaphospholan-2-one) present in the starting phosphonate. Proton NMR analysis (recorded in $CDCl_3$ solution at 400 MHz) verified that the carbon skeleton of this phosphonate was that required for synthesis of beta-carotene, et al. The latter spectrum exhibited two doublets (J=16 Hz) at δ 6.33 and 6.215 (C-4 and C-5 vinyl hydrogens), a multiplet at δ 4.14 ($POCH_2$), a singlet at δ 3.78 ($POCH_3$), a triplet (J=8 Hz) at δ 5 3.75 ($POCH_2$ C $\underline{H}_2OH$), and a doublet of doublets ($J_{H-H}$=8 Hz, $J_{P-H}$=23 Hz) at δ 2.79 ($CH_2P$).

What is claimed is:

1. An allenic phosphonate compound of the formula:

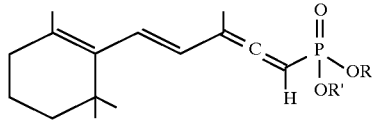

wherein R and R'=$C_1$–$C_4$ alkyl groups, or R, R'=$(CH_2)_n$ (n=2 or 3) or $[CH_2C(CH_3)_2CH_2]$.

2. The phosphonate of claim 1 which is:
3-methyl-5-(2,6,6-trimethyl-1-cyclohexen-1-yl)-1,2,4-pentatrienylphosphonic acid, diethyl ester.

3. The phosphonate of claim 1 which is:
3-methyl-5-(2,6,6-trimethyl-1-cyclohexen-1-yl)-1,2,4-pentatrienylphosphonic acid, dimethyl ester.

4. The phosphonate of claim 1 which is:
3-methyl-5-(2,6,6-trimethyl-1-cyclohexen-1-yl)-1,2,4-pentatrienylphosphonic acid, diisopropyl ester.

5. The phosphonate of claim 1 which is:
3-methyl-5-(2,6,6-trimethyl-1-cyclohexen-1-yl)-1,2,4-pentatrienylphosphonic acid, dipropyl ester.

6. The phosphonate of claim 1 which is:
3-methyl-5-(2,6,6-trimethyl-1-cyclohexen-1-yl)-1,2,4-pentatrienylphosphonic acid, dibutyl ester.

7. The phosphonate of claim 1 which is:
3-methyl-5-(2,6,6-trimethyl-1-cyclohexen-1-yl)-1,2,4-pentatrienylphosphonic acid, ethyl methyl diester.

8. The phosphonate of claim 1 wherein R and R' form part of a 5- or 6-membered heterocyclic ring.

9. The phosphonate of claim 8 which is:
2-[3-methyl-5-(2,6,6-trimethyl-cyclohex-1-enyl)penta-1,2,4-trienyl]-1,3,2-dioxaphospholan-2-one.

10. A method of preparing an allenic phosphonate compound of the formula:

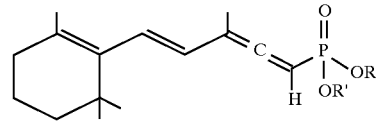

wherein R and R'=$C_1$–$C_4$ alkyl groups, or R, R'=$(CH_2)_n$ (n=2 or 3) or $[CH_2C(CH_3)_2CH_2]$
comprising the steps:
(I) forming a reaction mixture in an aprotic solvent comprising:
(a) ethynyl-β-ionol;
(b) at least one molar equivalent of a non-nucleophilic base; and
(c) at least one molar equivalent of a chlorophosphite reagent of the formula, $(RO)_2PCl$, wherein the R groups independently represent $C_1$ to $C_4$ alkyl or wherein the R groups, taken together, form part of a 5- or 6-member ring; and
(II) maintaining said reaction mixture until said allenic phosphonate is formed.

11. The method of claim 10 wherein said non-nucleophilic base is selected from the group consisting of:
tertiary amines, $Na_2CO_3$ and $K_2CO_3$.

12. The method of claim 11 wherein said tertiary amine is pyridine or triethylamine.

13. The method of claim 10 wherein said chlorophosphite reagent is selected from the group consisting of: diethyl chlorophosphite and 2-chloro-1,3,2-dioxaphospholane.

14. The method of claim 10 wherein said chlorophosphite reagent is added, dropwise, to a solution comprising ethynyl-β-ionol and at least one molar equivalent of a non-nucleophilic base in an aprotic solvent.

15. The method of claim 10 further including the step of adding water to said reaction mixture after formation of said allenic phosphonate compound to destroy any unreacted dialkyl chlorophosphite reagent.

16. The method of claim 10 wherein said allenic phosphonate compound is selected from the group consisting of:
3-methyl-5-(2,6,6-trimethyl-1-cyclohexen-1-yl)-1,2,4-pentatrienylphosphonic acid, diethyl ester;
3-methyl-5-(2,6,6-trimethyl-1-cyclohexen-1-yl)-1,2,4-pentatrienylphosphonic acid, dimethyl ester;
3-methyl-5-(2,6,6-trimethyl-1-cyclohexen-1-yl)-1,2,4-pentatrienylphosphonic acid, diisopropyl ester;
3-methyl-5-(2,6,6-trimethyl-1-cyclohexen-1-yl)-1,2,4-pentatrienylphosphonic acid, dipropyl ester;

3-methyl-5-(2,6,6-trimethyl-1-cyclohexen-1-yl)-1,2,4-pentatrienylphosphonic acid, dibutyl ester;

3-methyl-5-(2,6,6-trimethyl-1-cyclohexen-1-yl)-1,2,4-pentatrienylphosphonic acid, ethyl methyl diester; and 2-[3-methyl-5-(2,6,6-trimethyl-cyclohex-1-enyl)penta-1,2,4-trienyl]-1,3,2-dioxaphospholan-2-one.

17. A method of preparing a C-15 allylic phosphonate compound of the formula:

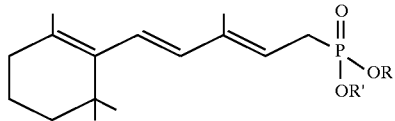

wherein R and R'=$C_1$–$C_4$ alkyl groups
comprising the steps:
(I) forming a first reaction mixture in an aprotic solvent comprising:
(a) ethynyl-β-ionol;
(b) at least one molar equivalent of a non-nucleophilic base; and
(c) at least one molar equivalent of a chlorophosphite reagent of the formula, $(RO)_2PCl$, wherein the R groups independently represent $C_1$ to $C_4$ alkyl or wherein the R groups, taken together, form part of a 5- or 6-member ring;

(II) maintaining said first reaction mixture until an allenic phosphonate is formed;

(III) forming a second reaction mixture in an alcohol solvent comprising the allenic phosphonate of step II, ammonium formate, and 10% Pd-C; and (IV) vigorously agitating said second reaction mixture while heating it to a temperature in excess of room temperature.

18. The method of claim 17 wherein said alcohol solvent of step III comprises methyl alcohol.

19. The method of claim 17 wherein said second reaction mixture is heated to a temperature between 60° C. and 65° C.

* * * * *

UNITED STATES PATENT AND TRADEMARK OFFICE
CERTIFICATE OF CORRECTION

PATENT NO. : 5,847,185
DATED : December 8, 1998
INVENTOR(S) : BABLER, James H.

It is certified that error appears in the above-identified patent and that said Letters Patent is hereby corrected as shown below:

Column 1, line 18    Reference Numeral -- (1) -- should be inserted centrally under the reaction.

Column 1, line 37    Reference Numeral -- (2) -- should be inserted centrally under the reaction.

Column 1, line 67    Reference Numeral -- (3) -- should be inserted centrally under the Part B: reaction.

Column 3, line 31    Reference Numeral -- (6) -- should be inserted centrally under the reaction.

Column 4, line 25    Reference Numeral -- (5) -- should be inserted centrally under the reaction.

Column 7, line 22    Delete the term "Dieth" and insert -- Diethyl Ester --.

Signed and Sealed this

Fifteenth Day of June, 1999

Attest:

Attesting Officer

Q. TODD DICKINSON

Acting Commissioner of Patents and Trademarks